United States Patent [19]
Wang et al.

[11] Patent Number: 5,739,539
[45] Date of Patent: Apr. 14, 1998

[54] USE OF BODY BOUNDARY INFORMATION TO PERFORM ITERATIVE RECONSTRUCTION IN MEDICAL IMAGING SYSTEM

[75] Inventors: Xiaohan Wang, Alameda; J. Keenan Brown, San Jose; Steven M. Jones, Pleasanton; John R. Liebig, San Jose, all of Calif.

[73] Assignee: ADAC Laboratories, Milpitas, Calif.

[21] Appl. No.: 625,533

[22] Filed: Mar. 27, 1996

Related U.S. Application Data

[60] Provisional application No. 60/004,365 Sep. 27, 1995.
[51] Int. Cl.$^6$ .................................................. G01T 1/166
[52] U.S. Cl. .................... 250/363.04; 250/363.02; 250/369
[58] Field of Search ................ 250/363.02, 363.03, 250/363.04, 370.09, 369

[56] References Cited

U.S. PATENT DOCUMENTS 4,984,159  1/1991  Gullberg .................................. 378/14
5,338,936  8/1994  Gullberg et al. .................. 250/363.04

*Primary Examiner*—David P. Porta
*Assistant Examiner*—David Vernon Bruce
*Attorney, Agent, or Firm*—Blakely, Sokoloff, Taylor & Zafman LLP

[57] ABSTRACT

A method of performing image reconstruction in a gamma camera system comprises the steps of performing a transmission scan of an object about a number of rotation angles to collect transmission projection data and performing an emission scan of the object about numerous rotation angles to collect emission projection data. The outer boundary of the object is then located based on the transmission projection data. Information identifying the boundary is then either stored in a separate body contour map or embedded in an attenuation map. The information identifying the boundary can be in the form of flags indicating whether individual pixels are inside or outside the boundary of the object. The emission projection data is then reconstructed, using the attenuation map if desired, to generate transverse slice images. By using the body boundary information, portions of the emission projection data representing points outside the boundary of the object are not reconstructed in order to reduce total reconstruction time.

22 Claims, 7 Drawing Sheets

USE OF BODY BOUNDARY INFORMATION TO PERFORM ITERATIVE RECONSTRUCTION IN MEDICAL IMAGING SYSTEM

The applicants of the present application claim the benefit under 35 U.S.C. § 119(e) of provisional U.S. Patent application no. 60/004,365, filed on Sep. 27, 1995.

FIELD OF THE INVENTION

The present invention pertains to the field of nuclear medicine imaging systems. More particularly, the present invention relates to a method and apparatus for performing iterative image reconstruction in a nuclear medicine imaging system.

BACKGROUND OF THE INVENTION

In nuclear medicine imaging techniques such as single-photon emission computed tomography (SPECT) and positron emission tomography (PET), medical images are generated based on gamma rays emitted from the body of a patient after the patient has been injected with a radiopharmaceutical substance. Emitted gamma rays are detected from numerous different projection angles around a longitudinal axis of the patient by a gamma camera (i.e., Anger camera or scintillation camera) and then converted into electrical signals that are stored as data. This data is then converted into a set of images in a process known as image "reconstruction".

Image reconstruction methods include both iterative methods, such as Maximum-Likelihood—Expectation-Maximization (ML-EM) and Least Squares (LS), as well as traditional (non-iterative) reconstruction methods, such as filtered back-projection (FBP). Iterative reconstruction methods often provide better image quality and more natural ways to incorporate attenuation correction than non-iterative methods. However, iterative methods are generally more computationally intensive and more time-consuming than non-iterative methods. In fact, iterative techniques can be on the order of ten times slower than non-iterative techniques. Consequently, iterative techniques are often unsuitable for clinical use. Hence, what is needed is a way to perform iterative image reconstruction in a nuclear medicine imaging system in a less computationally intensive, less time-consuming manner.

SUMMARY OF THE INVENTION

A method is provided of generating images in a gamma camera system. A transmission scan of an object is performed about a number of projection angles to collect transmission projection data. An emission scan of the object is also performed about numerous projection angles to collect emission projection data. Information locating a boundary of the object is located based on the transmission projection data. The emission projection data is then reconstructed to generate at least one image. In reconstructing the emission projection data, the information locating the boundary of the object is used to avoid reconstructing portions of the emission projection data that correspond to locations outside the boundary of the object.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
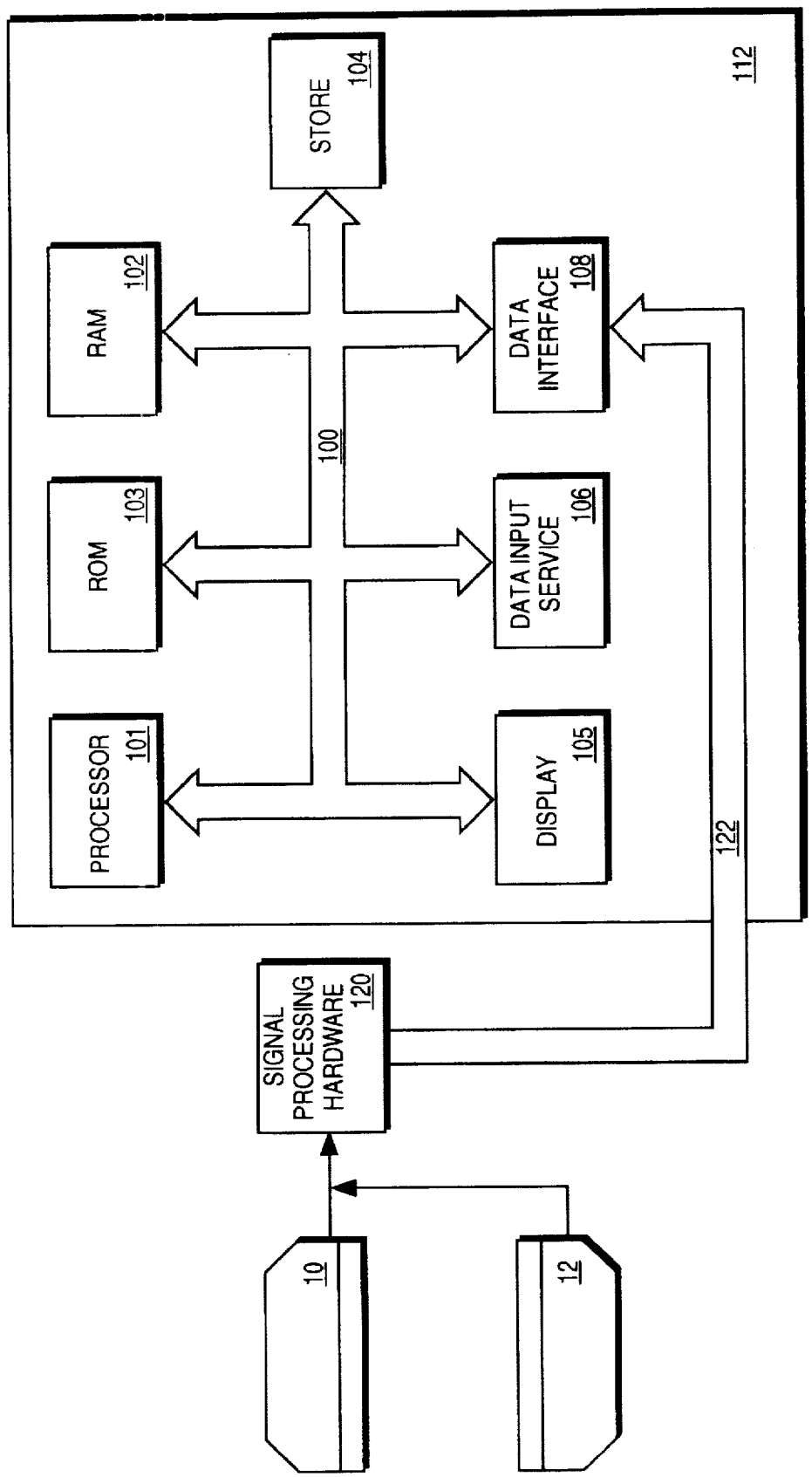
FIG. 1 is a block diagram a nuclear medicine imaging system.

A method is described of using body boundary information to speed up iterative image reconstruction in a medical imaging system. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to avoid unnecessarily obscuring the present invention. In the following description, unless specifically stated otherwise, discussions relating to functions of the computer system of the present invention utilizing terms such as "processing" or "computing" or "calculating" or "determining" or "displaying" or the like, refer to the action of a computer system, or similar electronic computing device, that is executing a program to manipulate and transform data represented as physical (electronic) quantities within the computer system's registers and memories into other data similarly represented as physical quantities within the computer system memories or registers.

According to the present invention, information locating the boundary of a patient's body is acquired and used to avoid reconstructing pixels corresponding to points outside the body in order to reduce overall reconstruction time, as will be described below. The present invention therefore applies the assumption that no significant emission radiation is generated outside the body.

As will be discussed below, certain embodiments of the present invention take advantage of techniques for performing attenuation correction to improve gamma camera imaging. Since each patient that is imaged by a nuclear medicine gamma camera has different physical characteristics (i.e., size, shape, etc.), the tissue and bone structure that surround an organ of interest is different for each patient. This surrounding tissue and bone structure attenuates the radiation emitted from a radiopharmaceutical distributed within the imaged organ. Attenuation can also be caused by other structures that are close to a patient's body during imaging, such as the table upon which the patient is placed. The attenuation caused by the body is generally nonuniform, because the attenuation coefficients of the different tissues and bone are different. Radiation attenuation non-uniformly reduces the count density in the image. This attenuation can lead to falsely identifying an artifact when in fact healthy tissue is imaged and vice-versa. If an artifact is improperly diagnosed as a lesion, this can lead to invasive measures which are painful and potentially dangerous (e.g., involves a health risk) for the patient. As a result, techniques have been developed to compensate for attenuation within the body as well as outside the body.

Attenuation caused by the body and nearby structures can be compensated for if an attenuation "map" is available. Some well-known methods of generating an attenuation map involve the use of transmission scanning. Transmission scanning allows a gamma camera and a processing computer system to generate an attenuation map of a particular object. Generally, during transmission scanning, a source of known radiation is transmitted through the patient, and the radiation is then detected by a scintillation detector. By knowing the intensity of the radiation transmitted from the source, and by measuring the intensity of radiation detected by the scintillation detectors at different projection angles, the gamma camera's computer system can determine the extent of radiation attenuation over different spatial locations. From this information, a nonuniform attenuation map of the body and nearby structures can be generated using well known methods and procedures, including filtered back-projection (FBP) reconstruction techniques. The nonuniform attenuation map can then be used during the reconstruction of emission projection data to correct emission image data collected during an emission scan.

Referring to FIG. 1, a nuclear medicine imaging system 1 in which the present invention can be implemented is illustrated in block diagram form. The system 1 includes a general purpose computer system 112 for processing image information supplied from gamma camera scintillation detectors 10 and 12. The computer system is coupled to scintillation detectors 10 and 12 by signal processing hardware 120. The computer system 112 is capable of processing both emission and transmission data collected by the detectors 10 and 12 in order to generate images. The computer system 112 also controls movement of the detectors on a gantry (not shown) in order to provide rotation of the detectors about a z (longitudinal) axis as well as relative translation along the z axis between the detectors 10 and 12 and a patient. The computer system 112 also controls and monitors movement of transmission line sources, which are discussed below.

Gamma rays impinging upon the detectors 10 and 12 cause scintillation events to occur within the detectors. The signal processing hardware 120 converts channel signals that are output by photomultiplier tubes (PMTs) within detectors 10 and 12 into spatial coordinate data and event energy for detected scintillation events. The signal processing hardware 120 includes amplification circuitry and analog-to-digital conversion circuits for converting the channel signals to digital data for transmission to the computer system 112.

The computer system 112 comprises a central processor 101; a random access memory 102; a read only memory 103; a data storage device 104, such as a magnetic or optical disk and disk drive; a display device 105 for displaying generated medical images to a user, such as a cathode ray tube (CRT) or a liquid crystal display (LCD); an input device 106, such as a keyboard or cursor control device, or both; and a data interface device 108 for communicating command selections to the processor 101. The above components are coupled together by a bus 100 for communicating information within the system 112. A printer or other equivalent output device may also be coupled to bus 100.

Channel signal information from the detectors 10 and 12 are converted into projection data by the computer system 112 and stored within the computer's memory 102 in matrix form. Detected scintillation events having similar spatial coordinates are "binned" together in the memory 102 of the computer system in order to generate image information and form count density information. Attenuation maps are also stored in memory 102.

Image information is collected in the form of a matrix of N rows by N columns. The size of the detector's effective field of view and the number of rows and columns of a particular matrix define the "size" of a pixel of the matrix. A pixel corresponds to one cell or "bin" of the matrix. Image matrices are generally collected at different projection angles, and a reconstruction is then performed. A series of two-dimensional transverse slice images may then be generated. A three-dimensional image may also be generated based on data representing multiple transverse slice images.

When data is received from a detector 10 or 12 regarding the energy and location of scintillation event, this information is "binned" (e.g., placed) into the appropriate matrix entry that corresponds to the location of the event as reported by the signal processing circuitry 120. For both transmission an emission modes, count information reported by the detectors is binned into memory 102, from which image data is generated.

Figure 2A:
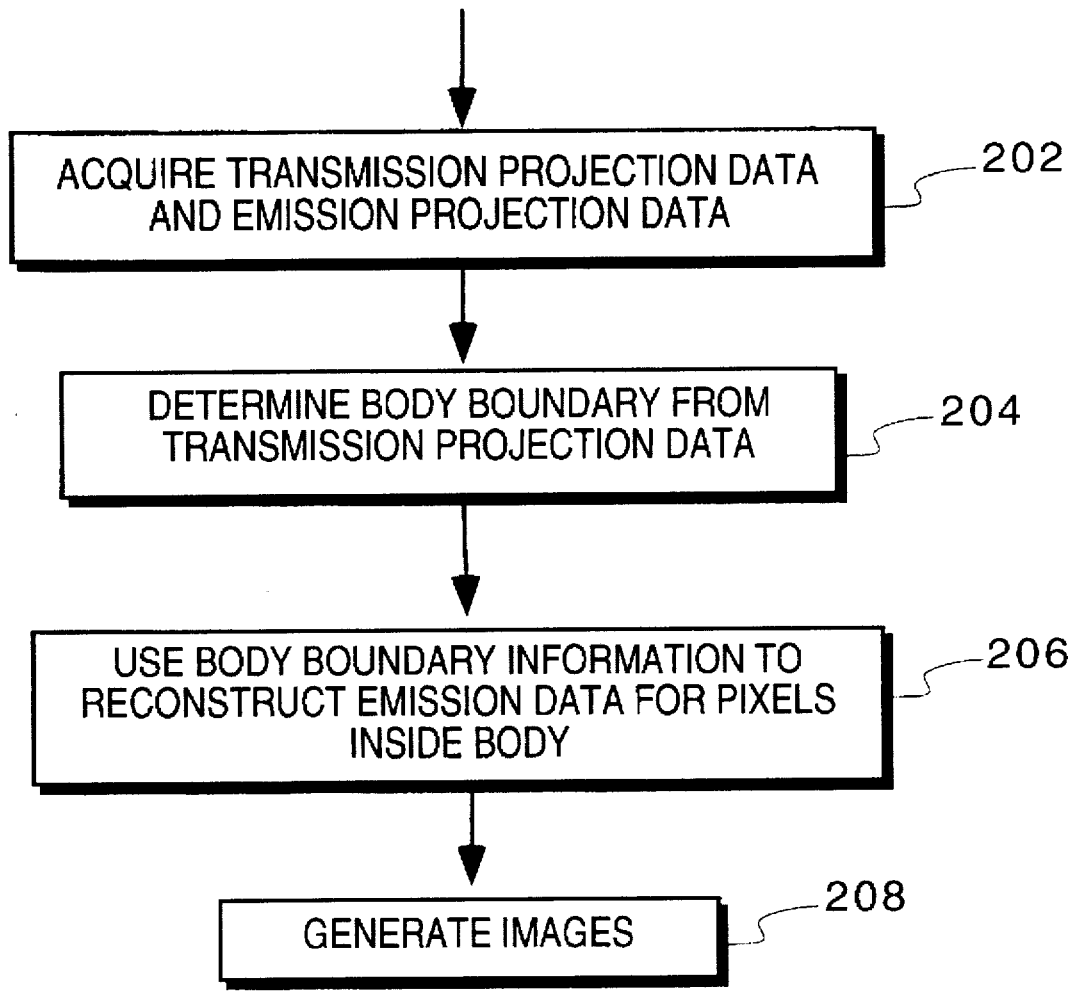
FIG. 2A is a flowchart illustrating the overall approach of the present invention.

FIG. 2A illustrates the overall approach of the present invention. Initially, transmission projection data and emission projection data are acquired (step 202). The outer boundary of the patient's body is then located from the acquired transmission projection data (step 204). Various techniques are known for locating objects represented in data and may be used for this purpose. Such techniques include algorithms based on edge detection, gradient detection, or threshold detection. Information identifying the location of the body boundary can be stored in various possible formats. For example, such information can be stored in a separate body contour map, or it can be embedded in an attenuation map. These formats are discussed further below. The body boundary information is then referred to and used during reconstruction of emission projection data to reconstruct only those pixels which correspond to points inside the body (step 206). In actual practice, some additional pixels corresponding to points outside the body may also be reconstructed to ensure that no inadvertent truncation occurs. The reconstructed image data is then used to display emission images (step 208).

Figure 3:
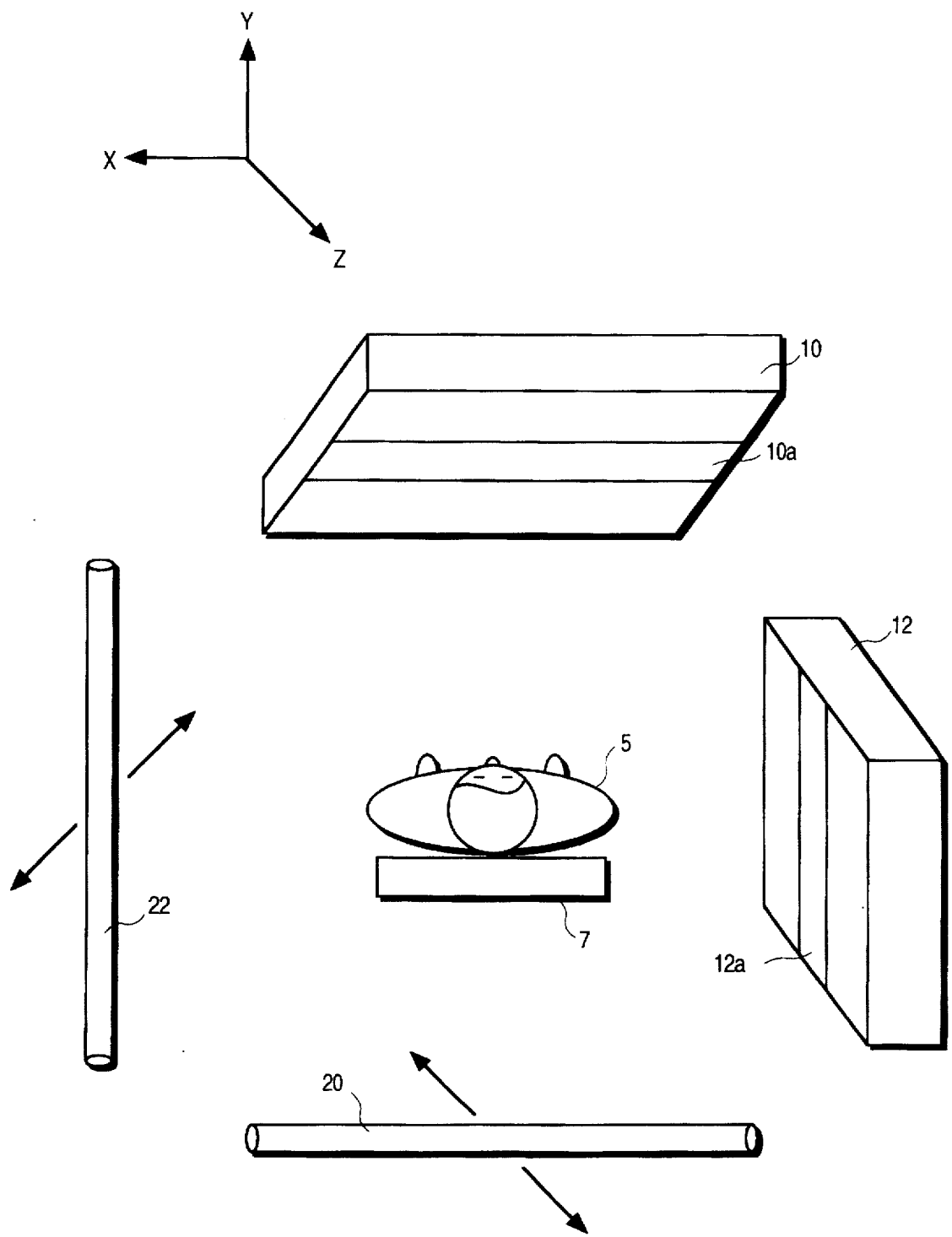
FIG. 3 illustrates an arrangement for performing a transmission scan on a patient.

FIG. 3 illustrates an arrangement for acquiring transmission data. In the preferred embodiment, transmission projection data and emission projection data are acquired simultaneously; however, transmission and emission data may instead be acquired in separate scans (as may be the case if PET imaging is desired). Separate energy levels may be used for emission and transmission modes to prevent interference between these two modes. In FIG. 3, a patient 5 rests upon a table 7 and is surrounded by two scintillation detectors 10 and 12 and two radiation line sources 20 and 22. Radiation transmitted by line source 20 is detected by detector 10, while radiation transmitted by line source 22 is detected by detector 12. Detectors 10 and 12 have large fields of view, such that there is no truncation of the complete image of the patient 5. Further, each of the detectors uses a parallel hole collimator (not shown) during the acquisition of transmission data. The detectors 10 and 12 and line sources 20 and 22 are rotated about the z axis through a range of angles sufficient to gather complete transmission projection data (i.e., data representing a range of 180 or more degrees around the z axis).

Figure 4:
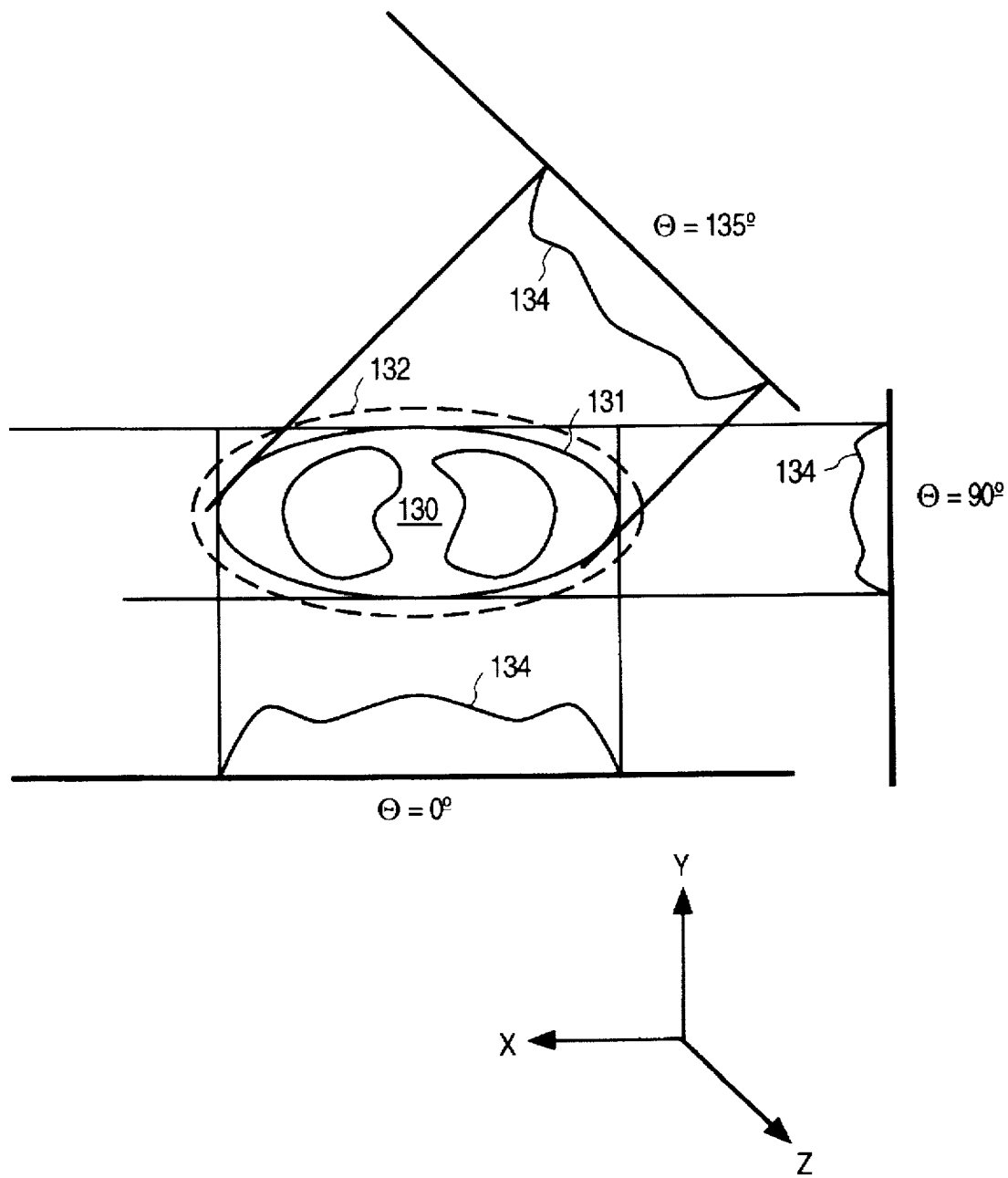
FIG. 4 illustrates an attenuation map generated from transmission projection data.

Once the body boundary is located from the transmission projection data, then for each transverse slice, a bounded area is determined which is just large enough so that it encompass slightly more than the patient's body. A margin of approximately 10 pixels, or 4 to 5 cm beyond the patient's body is currently considered sufficient for each transverse slice. FIG. 4 illustrates a transverse slice (perpendicular to the z axis) image 130 of the patient 5. The image 130 represents transmission projection data 134 acquired at various projection angles θ. A bounded area 132 can be determined from the data 134 which just encompasses the body boundary 131.

Once the bounded area is defined, information identifying this area is stored in an appropriate format. For example, the body boundary information can be stored in a separate body contour map. In one embodiment, the body contour map consists of a number of matrices, where each matrix corresponds to a different transverse slice. Each matrix of the body contour map consists of a number of binary values, each of which corresponds to a given point in space. For a given value in a matrix, if that value represents a point inside the bounded area 132, then it is assigned a predetermined binary value, whereas if the value corresponds to a point outside the bounded area 132, then the value is assigned the other binary value. During reconstruction of the emission projection data to generate emission images, the values in the body contour map are then examined and used to decide which pixels of the emission data to reconstruct.

Alternatively, the body boundary information may be embedded in an attenuation map. In one embodiment, a flag is set (step 210) in the attenuation map for each pixel representing a point outside the bounded area 132. An example of setting a flag is to modify the actual attenuation value by a numerical value which would not likely result from the actual data, such as adding or subtracting a very large constant (e.g., 1000) from the actual attenuation value. Using this technique, the attenuation information can be retained even for points outside the body, since the constant is a known value which can be subtracted or added out during attenuation correction, as appropriate.

In another embodiment in which the body boundary information is embedded in an attenuation map, setting a flag in the attenuation map to indicate a point outside the body may constitute simply replacing (rather than modifying) the actual attenuation value with a constant that is unlikely to occur in the actual data (such as −1000). A problem with this approach is that it assumes that no significant attenuation occurs outside the body, because the actual attenuation data is lost for points outside the body. As discussed above, that assumption is probably faulty, since nearby structures, such as the table 7 on which the patient is placed during imaging, generally cause measurable attenuation. Therefore, another alternative is to locate the boundary of the table 7 or other significant external attenuators using essentially the same techniques used to locate the body boundary; the bounded area 132 could then be defined to include any such external attenuators, such that attenuation information corresponding to points inside either the body or these other objects is not replaced.

Figure 2B:
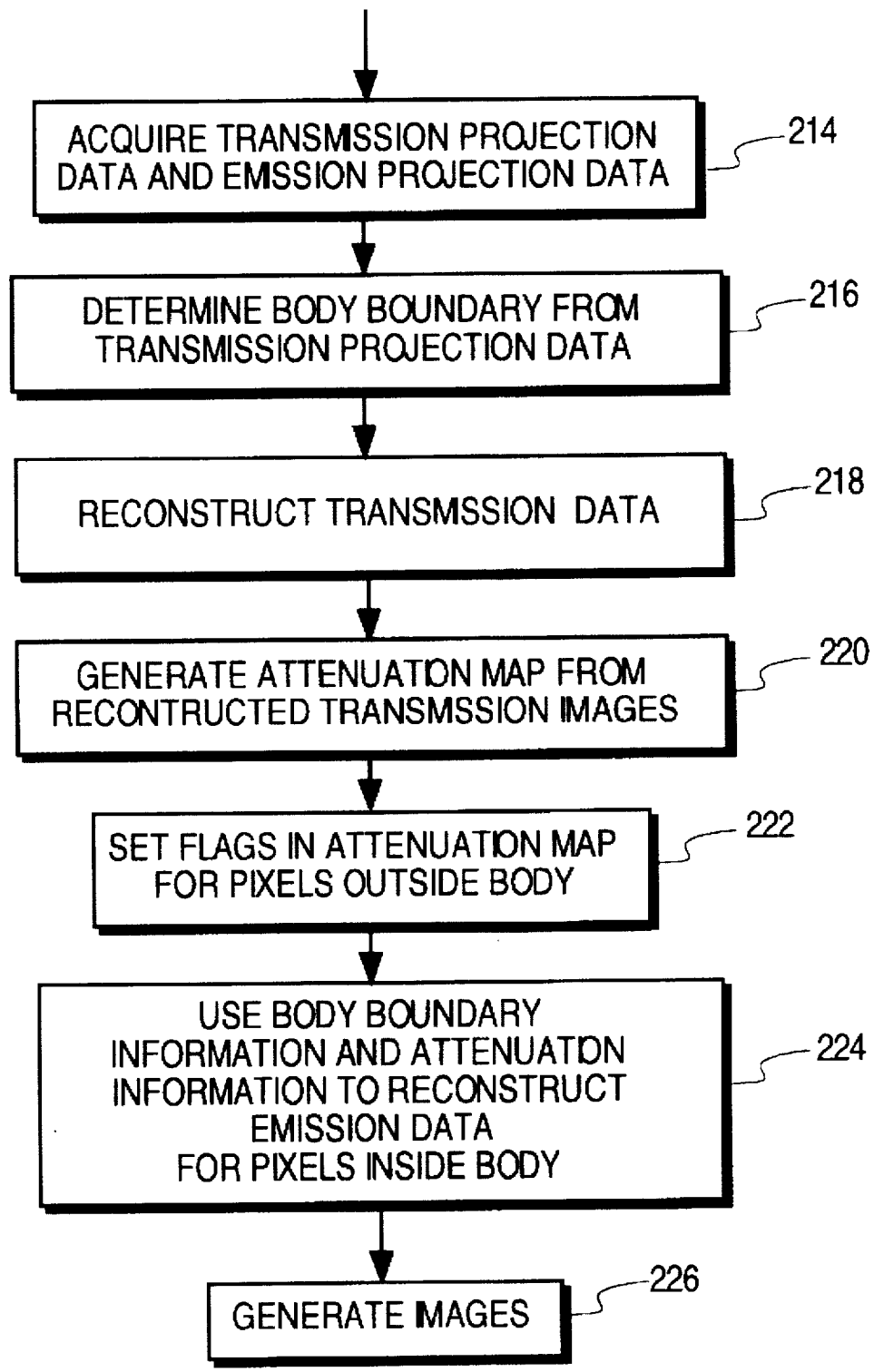
FIG. 2B is a flowchart illustrating a procedure according to the present invention, in which body boundary information is embedded in an attenuation map.

Referring now to FIG. 2B, a procedure is illustrated which makes use of an attenuation map in accordance with the present invention. First, transmission projection data and emission projection data are acquired (step 214). The outer boundary of the patient's body is then located from the acquired transmission projection data (step 216). After location of the body boundary from the transmission projection data, the transmission projection data is reconstructed (step 218) using filtered back-projection (FBP) and normalized using a previously acquired "reference scan". An attenuation map 130 is generated from the reconstructed transmission data using well-known techniques (step 220). Flags are then set in the attenuation map (step 222) to indicate the location of the body boundary, or more specifically, the bounded area which just encompasses the body boundary (see FIG. 4 and corresponding discussion). The emission projection data is then reconstructed (step 224) using an iterative reconstruction technique, in conjunction with the body boundary information and the attenuation information, to reconstruct only those pixels representing points inside the bounded area while correcting for attenuation. Emission images are then generated from the reconstructed data (step 226).

Figure 5:
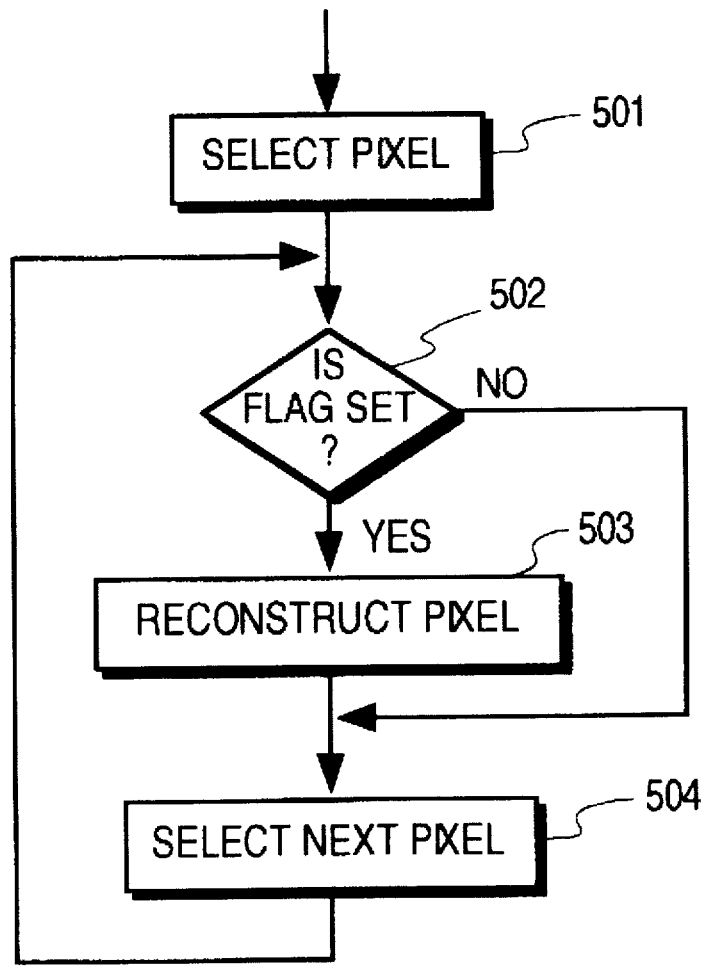
FIG. 5 illustrates a flowchart of the process for reconstructing emission data based on body boundary information embedded in an attenuation map.

FIG. 5 illustrates an iterative reconstruction procedure according to the present invention. First, a pixel corresponding to emission projection data is selected for reconstruction (step 501). Next, a determination is made of whether a flag has been set for that pixel in the body boundary information (step 502). Again, the body boundary information may be stored in any appropriate format, such as a separate body contour map or embedded in an attenuation map. In a separate body contour map, the flag may simply be a predetermined binary value. If a flag has not been set, the pixel corresponds to a point inside the bounded area 132, and that pixel is reconstructed using an iterative algorithm (step 503). Otherwise, the pixel represents a point outside the bounded area 132, and that pixel is not reconstructed; accordingly, the next pixel is selected (step 504). The above process is repeated until all pixels have been examined. Attenuation data may also be used in reconstructing the emission images, as noted above.

Figure 6:
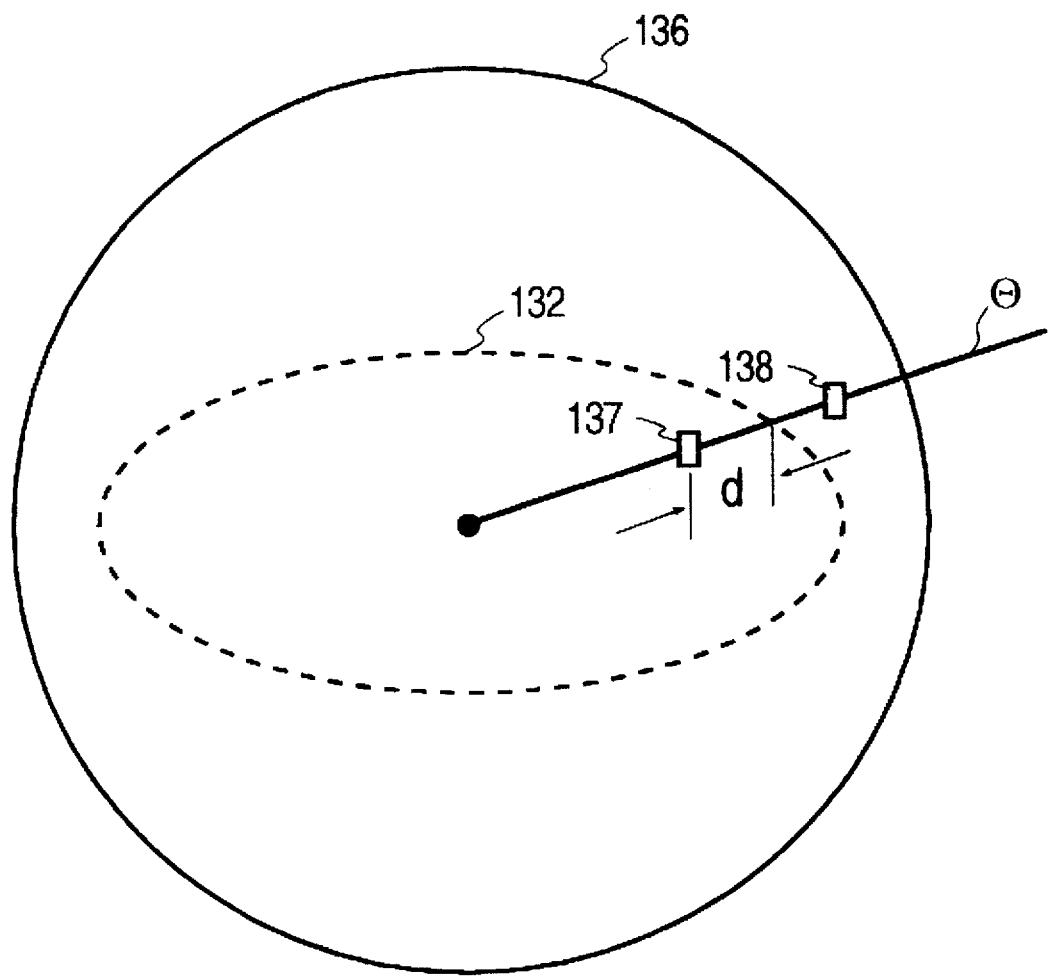
FIG. 6 illustrates a comparison of areas reconstructed both with and without using the reconstruction technique of the present invention.

Thus, referring to FIG. 6, the area 136 represents the area which would be reconstructed without implementing the technique of the present invention. In contrast, the area 132 represents the area that is reconstructed by applying the technique of the present invention. Pixel 137, for example, which lies within the bounded area 132, is reconstructed, whereas pixel 138 is not reconstructed. If significant external attenuators (such as the table 7) are included in the bounded area 132, then for a given projection angle θ, attenuation correction is performed when reconstructing pixel 137 by integrating the attenuation over the distance 'd' between the location of pixel 137 and the location of the boundary of the bounded area 132 at that projection angle θ. The distance 'd' is determined based on the flags in the attenuation map. It will be apparent, therefore, that because a substantially smaller area is reconstructed than would be otherwise, the present invention provides a reduction in the overall reconstruction time.

Thus, a method of reducing overall reconstruction time for iterative reconstruction techniques by using body boundary information has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of generating images in a gamma camera system, comprising the steps of:
    performing a transmission scan of an object about a plurality of projection angles to collect transmission projection data;
    performing an emission scan of the object about a plurality of projection angles to collect emission projection data;

generating information locating a boundary of the object based on the transmission projection data; and reconstructing the emission projection data to generate at least one image, including using the information locating a boundary of the object to avoid reconstructing portions of the emission projection data that correspond to locations outside the boundary of the object.

2. A method according to claim 1, further comprising the step of generating an attenuation map.

3. A method according to claim 2, wherein the step of generating information locating a boundary of the object comprises the step of generating a body boundary map separate from the attenuation map.

4. A method according to claim 2, further comprising the step of including the information locating a boundary of the object in the attenuation map.

5. A method according to claim 4, wherein the attenuation map includes a plurality of attenuation values, and wherein the step of including the information locating a boundary of the object in the attenuation map includes the step of modifying by a predetermined quantity certain ones of the attenuation values which correspond to positions outside the boundary of the object.

6. A method according to claim 1, wherein in the step of reconstructing comprises the step of using an iterative reconstruction technique to reconstruct the emission projection data to generate said at least one image.

7. A method of generating images in a gamma camera system, comprising the steps of:

performing a transmission scan of an object about a plurality of projection angles to collect transmission projection data;

performing an emission scan of the object about a plurality of projection angles to collect emission projection data;

generating an attenuation map from the transmission projection data;

locating a boundary of the object based on the transmission projection data;

including information identifying the boundary of the object in the attenuation map; and reconstructing the emission projection data using the attenuation map to generate at least one image, the reconstructing step including the step of using the information identifying the boundary of the object to avoid reconstructing portions of the emission projection data that correspond to locations outside the boundary of the object.

8. A method according to claim 7, wherein the step of generating the attenuation map comprises the step of generating data representing at least one transverse slice, and wherein the step of locating comprises the step of, for each transverse slice, determining a bounded area encompassing the boundary of the object.

9. A method according to claim 7, wherein the step of reconstructing comprises the step of using an iterative reconstruction technique to reconstruct the emission projection data to generate said at least one image.

10. A method according to claim 7, wherein the step of including comprises the step of setting a plurality of flags within the attenuation map to indicate the boundary.

11. A method according to claim 7, wherein:

the step of generating an attenuation map comprises the step of determining a plurality of attenuation values; and the step of including information locating the boundary of the object in the attenuation map comprises the step of modifying certain ones of the values within the attenuation map which correspond to positions outside the boundary of the object by a predetermined constant.

12. A method of generating images in a nuclear medicine imaging system, comprising the steps of:

performing a transmission scan of an object about a plurality of projection angles to collect transmission projection data;

performing an emission scan of the object about a plurality of projection angles to collect emission projection data;

generating an attenuation map from the transmission projection data;

generating a body contour map based on the transmission projection data, the body contour map including a plurality of flags identifying the boundary of the object; and reconstructing the emission projection data using the attenuation map and the body contour map to generate at least one image, the emission projection data corresponding to a plurality of pixels, the reconstructing step including the steps of:

for each pixel, examining a corresponding flag in the body contour map; and if the corresponding flag is not set, reconstructing said pixel using the attenuation map; and if the corresponding flag is set, not reconstructing said pixel; such that portions of the emission projection data that correspond to locations outside the boundary of the object are not reconstructed in generating said at least one image.

13. A nuclear medicine imaging system comprising:

a radiation detector;

a transmission source of radiation;

a processor coupled to the radiation detector and the transmission source, the processor configured to control the transmission source and the radiation detector to perform a transmission scan of an object about a plurality of projection angles and to collect transmission projection data therefrom;

the processor further configured to control the radiation detector to perform an emission scan of the object about a plurality of projection angles and to collect emission projection data therefrom;

the processor further configured to generate an attenuation map from the transmission projection data;

the processor further configured to locate a boundary of the object based on the transmission projection data;

the processor further configured to include information locating the boundary of the object in the attenuation map; and the processor further configured to reconstruct the emission projection data using the attenuation map to generate at least one image, the processor further configured to use the information locating the boundary of the object to avoid reconstructing portions of the emission projection data that correspond to locations outside the boundary of the object; and a memory coupled to the processor to store and provide access to the transmission projection data, the emission projection data, and the attenuation map.

14. A nuclear medicine imaging system according to claim 13, wherein the processor is further configured to generate the attenuation map comprising at least one transverse slice, and wherein the processor is further configured to, for each transverse slice, determine a bounded area encompassing the boundary of the object.

15. A nuclear medicine imaging system according to claim 13, wherein the processor is further configured to reconstruct the emission projection data using an iterative reconstruction technique.

16. A nuclear medicine imaging system according to claim 13, wherein the processor is further reconfigured to set a plurality of flags within the attenuation map to indicate the boundary.

17. A gamma camera system comprising:

a radiation detector;

a transmission source of radiation;

a processor coupled to control the radiation detector and the transmission source to perform a transmission scan of an object about a plurality of projection angles to collect transmission projection data;

the processor further configured to control the detector to perform an emission scan of the object about a plurality of projection angles to collect emission projection data;

the processor further configured to generate an attenuation map from the transmission projection data, the attenuation map including at least one transverse slice;

the processor further configured to generate information locating a boundary of the object based on the transmission projection data; and the processor further configured to reconstruct the emission projection data to generate at least one image, including using the information locating a boundary of the object to avoid reconstructing portions of the emission projection data that correspond to locations outside the boundary of the object.

18. A gamma camera system according to claim 17 wherein the processor is further configured to generate an attenuation map from the transmission projection data.

19. A gamma camera system according to claim 18, wherein the processor is configured to organize the information locating a boundary of the object in a body boundary map separate from the attenuation map.

20. A gamma camera system according to claim 18, wherein the processor is configured to include the information locating a boundary of the object in the attenuation map.

21. A gamma camera system according to claim 20, wherein the attenuation map includes a plurality of attenuation values, and wherein the processor is further configured to include the information locating a boundary of the object in the attenuation map by modifying by a predetermined quantity certain ones of the attenuation values which correspond to positions outside the boundary of the object.

22. A method according to claim 17, wherein in the step of reconstructing comprises the step of using an iterative reconstruction technique to reconstruct the emission projection data to generate said at least one image.

* * * * *